United States Patent [19]

Kikuchi et al.

[11] Patent Number: 4,656,650
[45] Date of Patent: Apr. 7, 1987

[54] X-RAY DIAGNOSTIC APPARATUS FOR ELIMINATING SCATTERED X-RAY COMPONENTS

[75] Inventors: Katsuya Kikuchi; Michitaka Honda, both of Tochigi, Japan

[73] Assignee: Kabushiki Kaisha Toshiba, Kawasaki, Japan

[21] Appl. No.: 719,168

[22] Filed: Apr. 2, 1985

[30] Foreign Application Priority Data

Apr. 3, 1984 [JP] Japan ................................. 59-66259

[51] Int. Cl.$^4$ ........................ H05G 1/64; G01N 23/00
[52] U.S. Cl. ............................................ 378/7; 378/99
[58] Field of Search ................ 378/7, 70, 154, 99, 378/145, 147

[56] References Cited

U.S. PATENT DOCUMENTS 4,286,156  8/1981  Wagner ................................. 378/7
4,380,818  4/1983  Pfeiler ................................. 378/99
4,549,307  10/1985  Macovski ............................. 378/7

*Primary Examiner*—Janice A. Howell
*Attorney, Agent, or Firm*—Finnegan, Henderson, Farabow, Garrett & Dunner

[57] ABSTRACT

In an X-ray diagnostic apparatus, it is very desirable to mitigate the adverse effect of the scattered X-ray components. When the X-ray shield member is positioned in the X-ray projection area during the first X-ray projection period, the first X-ray transmission image data is obtained. From this X-ray transmission image data, the scattered X-ray component data is calculated in the interpolation method of a SINC function. When the X-ray shield member is removed from the X-ray projection area during the second X-ray projection period, the second X-ray transmission image data is obtained that includes not only the primary X-ray components but also the scattered X-ray components. The desirable X-ray transmission image data is obtained by subtracting the first image data from the second image data.

7 Claims, 16 Drawing Figures

UNSHIELDED X-RAY IMAGE DATA

FIG. 6C

SHIELDED X-RAY IMAGE DATA

FIG. 6D

PRIMARY X-RAY INTENSITY DATA FOR SHIELDED AREAS

FIG. 6E

BILEVEL QUANTIZATION

FIG. 12 ns of the bilevel quantization;

X-RAY DIAGNOSTIC APPARATUS FOR ELIMINATING SCATTERED X-RAY COMPONENTS

BACKGROUND OF THE INVENTION

I. Field of the Invention

This invention generally relates to an X-ray diagnostic apparatus in which a transmitted X-ray image of an object under examination, e.g., a patient, is available for diagnostic purposes, and more particularly, to an X-ray diagnostic apparatus by which visible X-ray images of the object can be obtained, based only upon primary X-rays, without any adverse influences caused by the scattered X-rays.

II. Background Information

Generally, in the X-ray diagnostic apparatus set forth in the preamble, X-rays incident on an X-ray detector through the object under examination such as a patient contain not only primary X-rays but also X-rays which have been scattered by the object. The scattered X-rays constitute one of the major causes of deteriorated contrast and resolution in the transmitted X-ray image. This makes it necessary to eliminate the scattered X-ray components from the transmitted X-ray image data as provided by the X-ray detector.

One of the approaches to eliminate the scattered X-ray components is to use a so-called "Buckey Blade" or an elimination grid for the scattered X-rays (referred to as a "grid"). This approach involves a new problem in that there is a limit in the scattered X-ray elimination, because the grid per se produces the scattered X-rays incident thereupon.

The elimination of the scattered X-rays is very significant in the field of the X-ray diagnosis for the reasons that it improves an X-ray image quality, such as contrast and resolution, and thus allows a logarithm conversion of primary X-rays image data, thereby obtaining an accurate attenuation quantity of X-rays caused by the object when the X-rays pass through the object. Many studies have been made on the scattered X-rays, aiming at their effective elimination. The complicated phenomena of the scattered X-rays impede or almost reject a theoretical approach to this theme.

U.S. Pat. No. 4,549,307 reports a technique which establishes a total scatter radiation signal and then subtracts the total scatter radiation signal from the detected radiation signal. The scatter radiation signal is established by shielding portions of the detector and measuring radiation at the shielded portions of the detector to obtain a partial scatter radiation signal. The total scatter radiation signal is then reported to be interpolated from spatial distribution of the partial scatter radiation signal measured at the shielded areas.

SUMMARY OF THE INVENTION

For the above background reasons, an object of the present invention is to provide, by introducing a novel technical idea, an improved X-ray diagnostic apparatus which can effectively eliminate the scattered X-ray image components from the transmitted X-ray image components as obtained by the X-ray detector.

The object of the present invention may be accomplished by providing an X-ray diagnostic apparatus comprising:

an X-ray source for generating X-rays;

an X-ray detector for detecting an X-ray image of an object under observation by projecting X-rays from the X-ray source toward the object over an X-ray projection area and for converting a resultant detected image into X-ray transmission signals;

an analog-to-digital converter for converting the X-ray transmission signals into corresponding digital X-ray transmission data;

an X-ray shield member having a plurality of X-ray shields for selectively blocking the transmission of the X-rays from the X-ray source to the X-ray detector through the object for selected blocked portions of the projection area;

a first memory for temporarily storing first X-ray transmission data acquired from the analog-to-digital converter with the X-ray shield member inserted into the X-ray projection area;

a second memory for temporarily storing second transmission data acquired from the analog-to-digital converter with the X-ray shield member removed from the X-ray projection area; and arithmetic operation means:

i. for performing a first subtraction between the first X-ray transmission data and the second X-ray transmission data to obtain first X-ray intensity data of the selected blocked portions of the projection area which are shielded by the X-ray shield;

ii. for performing bilevel quantization of the first X-ray intensity data to obtain bilevel data which identifies those portions of the first X-ray transmission data corresponding to the selected block portions of the projection area;

iii. for obtaining, as a function of the bilevel data, selected data from the selected block portions of the first X-ray transmission data;

iv. for interpolating the selected data over the projection area; and v. for performing a second subtraction between the second X-ray transmission data and the interpolated selected data to obtain third X-ray transmission data essentially free from scattered X-ray components.

BRIEF DESCRIPTION OF THE DRAWINGS

This and other objects and features of the present invention may be best understood by reference to the specification and the accompanying drawings, in which.

DETAILED DESCRIPTION OF THE PREFERRED EMBODIMENTS

A detailed description of the invention, as given in this specification, is organized in accordance with the following index which is presented for the convenience of the reader.

1. PRINCIPLE BACKGROUND OF INVENTION
2. ARRANGEMENT OF THE APPARATUS
3. X-RAY SHIELD MEMBER
4. OPERATION OF THE APPARATUS
5. BILEVEL QUANTIZATION
6. CALCULATION OF SCATTERED X-RAY
7. FUNCTIONS OF ARITHMETIC OPERATION DEVICES
8. DETAILED OPERATION OF 3RD ARITHMETIC OPERATION DEVICE
9. INTERNAL CIRCUIT DIAGRAM OF 3RD ARITHMETIC OPERATION DEVICE
10. ENTIRE OPERATION OF EMBODIMENT
11. PRACTICAL CIRCUIT OF 3RD ARITHMETIC OPERATION DEVICE

1. PRINCIPLE BACKGROUND OF INVENTION

First, a description is made of the phenomenon scattered X-rays.

It is assumed that X-rays incident on the object under examination such as a patient are generally classified into primary X-rays which directly transmit through the object and enter into an X-ray detector, and X-rays absorbed or scattered by the object through interactions of the X-rays with atoms constituting the object. Those scattered ones are called "scattered X-rays". In the energy range of medical X-rays (radiated under 50 KVp to 120 KVp of the X-ray tube voltage), some causes for the scattered X-rays are known, for example, photoelectric effects, Compton effects, Thomson effects, and the like. These phenomena cooperate to cause the scattered X-rays to have adverse effects on the transmitted X-ray image (which will be described later). In general, because the scattered X-rays incident on the X-ray detector experience multi-scattering within the object, it is very difficult to exactly grasp an intensity and a spatial spread of an incident X-ray beam. This phenomenon is explained as follows.

Figure 1:
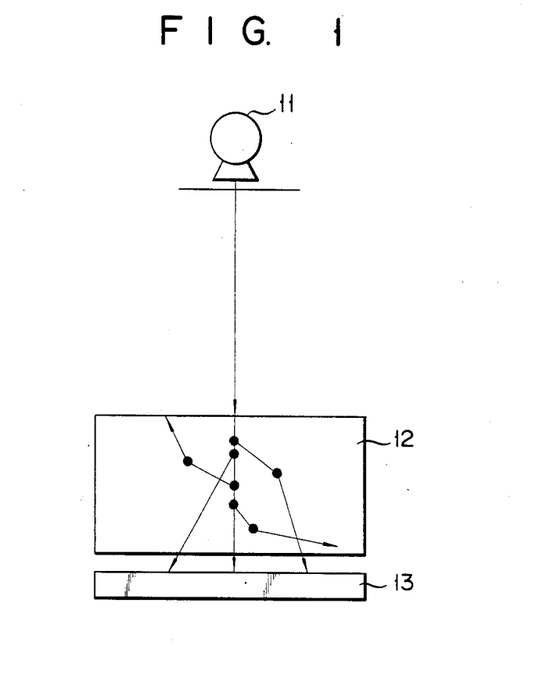
FIG. 1 is an illustration for explaining an occurrence of scattered X-rays when an X-ray is projected toward an object under examination.
Figure 2:
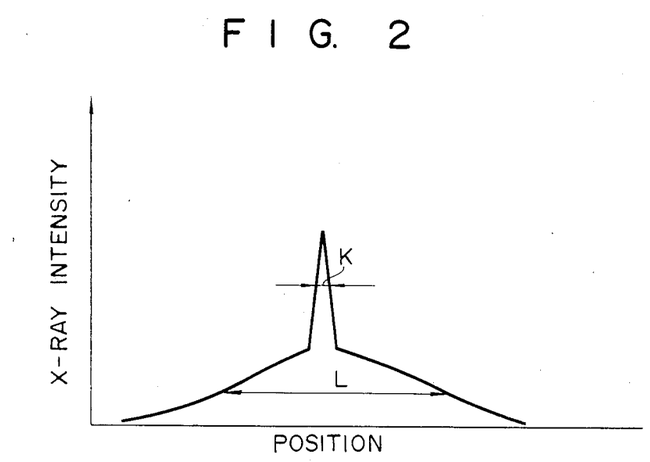
FIG. 2 shows a graphic representation on an X-ray intensity vs., a detection position on an X-ray detector.

FIG. 1 schematically illustrates how an X-ray radiated from an X-ray source 11 such as an X-ray tube, is scattered within an object 12, under examination and reaches an X-ray detector 13, while depicting a spatial spread with respect to the detecting positions of the X-ray detector. FIG. 2 illustrates an X-ray intensity distribution over the detecting positions of the X-ray detector 13. As seen from FIG. 2, a narrow spread, or spatial distribution of a sharp peak (as indicated by character K), located substantially at the center of the distribution curve, is caused by an inherent matter of the diagnosis system, for example, an X-ray focal spot and a wide spread (as indicated by character L) is caused by the scattered X-rays.

Figure 3A:
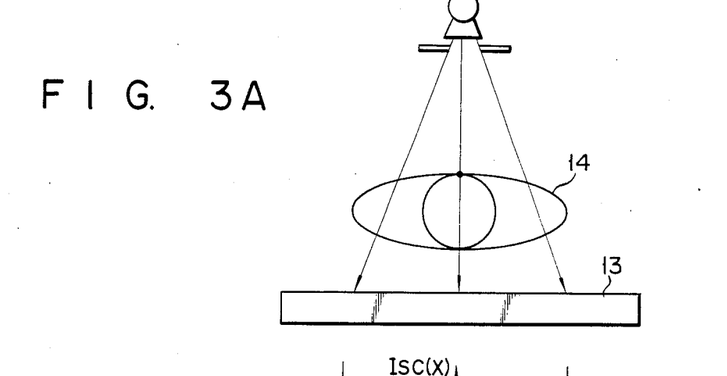
FIGS. 3A, 3B and 3C graphically illustrate a spatial distribution of the scattered X-rays' intensity.
Figure 3B:
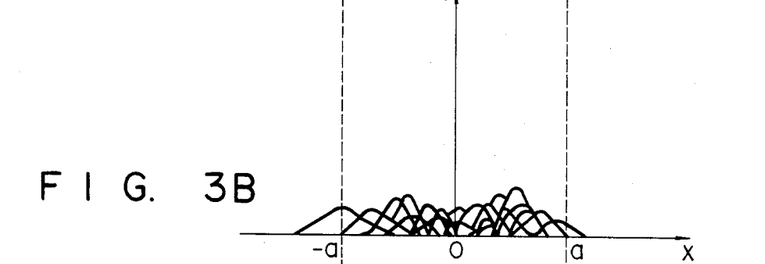
Figure 3C:
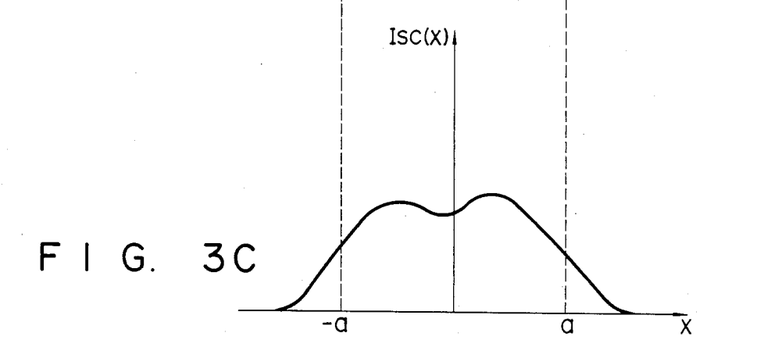

In FIG. 3, a spatial distribution of the scattered X-rays is graphically shown. In FIG. 3A, a narrow X-ray beam is projected toward a body 14. In FIG. 3B, spatial distributions of the respective scattered X-rays are graphically shown. In FIG. 3C, an actual spatial distribution of the scattered X-rays is graphically shown, that is obtained by summing these spatial distributions. The characters "−a" and "a" define an area projected by the X-rays (referred to as an "X-ray projection area") on the detecting positions of the X-ray detector 13. The symbol "Isc(x)" denotes an intensity of the scattered X-rays in the X-direction. For convenience and clarity of illumination, these drawings are illustrated in one dimension.

A total X-ray intensity distribution Im(x, y) incident on the detector 13 is the sum of the primary X-ray intensity distribution Ip(x, y) and the scattered X-rays intensity distribution Isc(x, y) and is given by:

$$Im(x, y) = Ip(x, y) + Isc(x, y) \qquad (1).$$

where (x, y) indicates coordinates for representing positions on the X-ray detector 13.

As previously described, since the spatial distributions of the scattered X-ray components Isc(x, y) gradually vary over the X-ray projection area, it is practically possible to relatively, precisely estimate the scattered X-ray component Isc(x, y) over the X-ray projection area by employing a plurality of the scattered X-ray component data.

The basic idea of the present invention can be realized based upon the above-described recognition.

In accordance with the basic idea of the present invention, the X-rays are successively projected toward the object under examination in such a way that an X-ray shield member is interposed between the X-ray source and the X-ray detector within the X-ray projection area. The X-ray projection area is defined by projecting the X-ray from the X-ray source to the X-ray detector through the object. Under such a condition, shielded X-ray image data is obtained by the detector which contains the scattered X-ray components only in the shielded portions, because the primary X-ray components in the shielded portions have been shielded by the X-ray shield member before reaching the X-ray detector. The scattered X-ray components of the shielded areas may be obtained from the shielded X-ray image data in accordance with the teachings of the subject invention. These components are referred to as X-ray shielded data. By interpolating the X-ray shielded data over the entire projection area, scattered X-ray intensity data for the entire projection area may be obtained. Unshielded X-ray image data is acquired under the condition that the X-ray shield member is removed from the X-ray projection area. Accordingly, the unshielded X-ray image data contains not only the scattered X-ray components but also the primary X-ray components. As a result, subtracting the scattered X-ray intensity data from the unshielded X-ray image data enables desirable image data to be calculated in accordance with the above equation 1. This desirable image data involves only the primary X-ray components.

2. ARRANGEMENT OF THE APPARATUS

Figure 4:
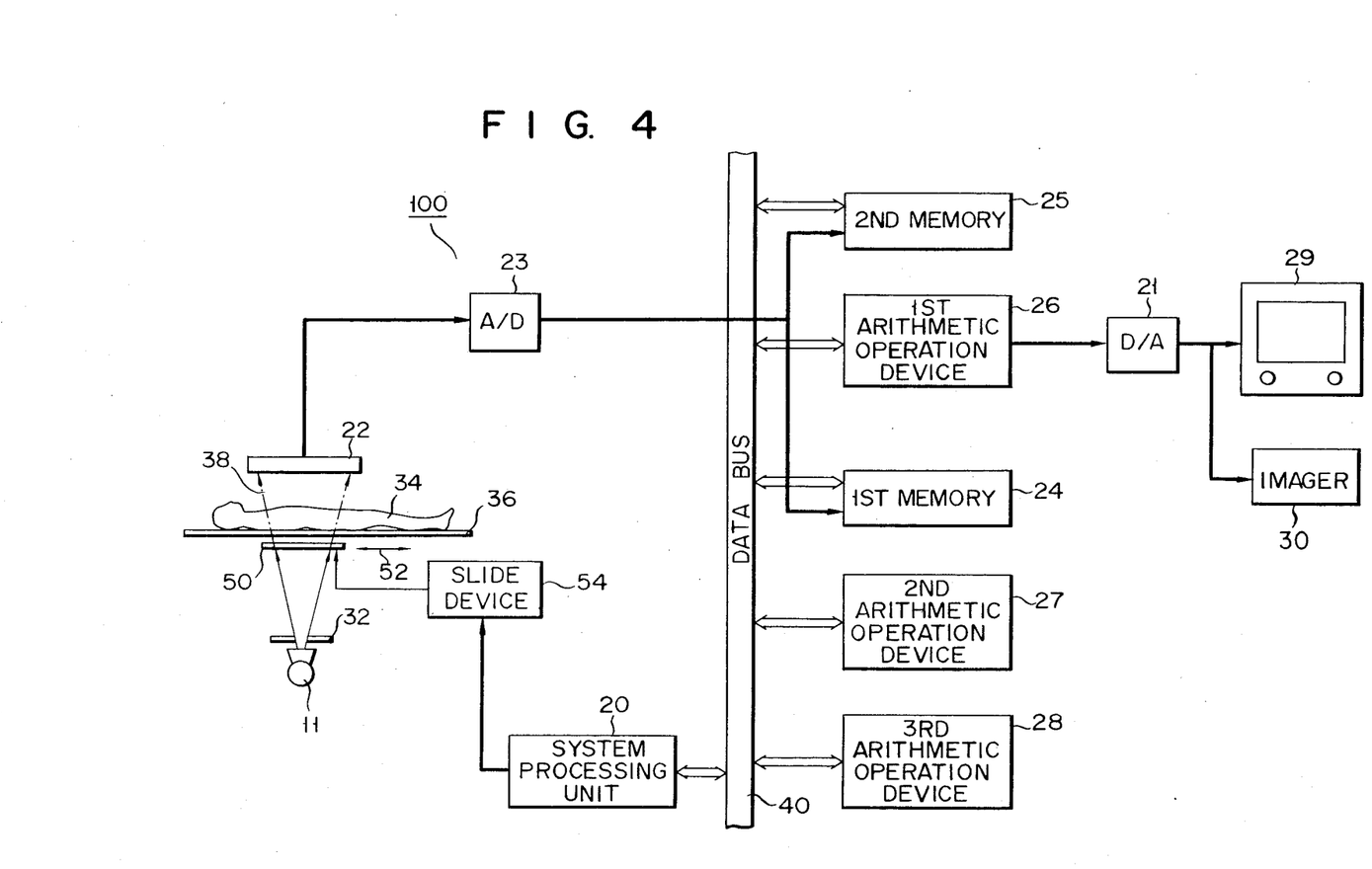
FIG. 4 shows a schematic block diagram of an X-ray diagnostic apparatus according to one preferred embodiment of the present invention.

Referring to FIG. 4, a description is made of an X-ray diagnostic apparatus 100 according to the preferred embodiment, in which the above basic idea has been employed.

An X-ray source 11 generates X-rays that are projected through a collimator 32 toward a patient 34 under examination. The patient 34 lies down on a couch 36. The X-ray projection area of the X-ray source 11 which is defined by the collimator 32 is denoted by reference numeral 38, that is defined by projecting the X-ray from the X-ray source 11 to the X-ray detector 22 through the patient 34.

An X-ray shield member 50 is provided under the couch 36. In other words, it is positioned in front of the patient 34 along the X-ray transmission path. This shield member 50 is designed to be slidable in parallel to the patient 34 or the couch 36. The slide operation into the X-ray projection area 38 will be described later. A slide direction is indicated by an arrow 52.

A system processing unit 20 is provided with the X-ray diagnostic apparatus 100. A slide device 54 allows to mechanically slide the X-ray shield member 50 along the slide direction 52 under the control of the system processing unit 20. An X-ray detector 22 such as an image intensifier is positioned behind the patient 34 along the X-ray transmission path within the X-ray projection area 38. Outputs of the detector 22 are fed to an analogue-to-digital converter (A/D converter) 23. To the A/D converter 23, first and second memories 24, and 25 are connected. The first memory 24 is mainly communicated with a first arithmetic operation device 26 and the second memory 25 is communicated with a second arithmetic operation device 27.

A third arithmetic operation device 28 is communicated with the first memory 25 via the data bus 40. The output of the first arithmetic operation device 26 communicated with the second arithmetic operation device 27 is connected via a digital-to-analogue converter 21 to a TV monitor 29 and also an imager 30 which optically records the X-ray images on X-ray films. The first and second memories 24, 25 and the first to third arithmetic operation devices 26 to 28 and the other circuit elements are controlled via a control line (not shown) by the system processing unit 20.

3. X-RAY SHIELD MEMBER

Figure 5:
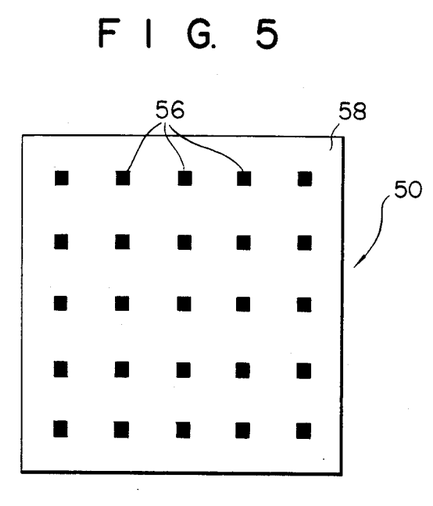
FIG. 5 schematically shows a front view of an X-ray shield member.
Figure 6A:
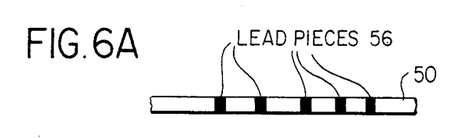
FIGS. 6A, 6B and 6C graphically illustrate operations of the bilevel quantization.
Figure 6B:
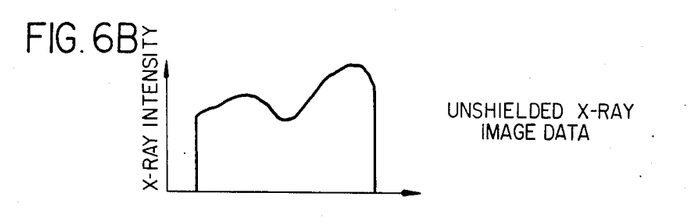
Figure 6C:
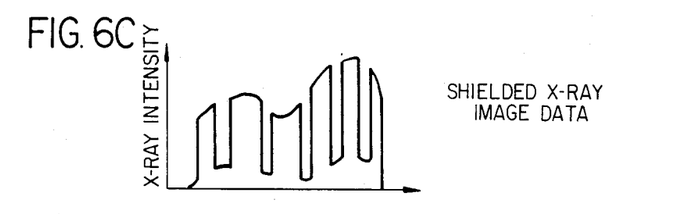
Figure 6D:
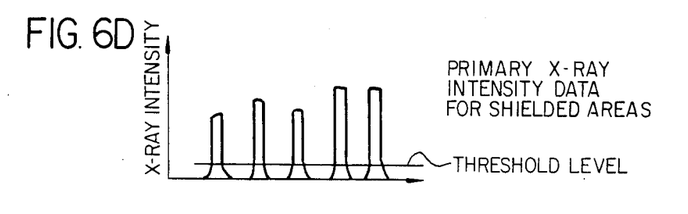
Figure 6E:
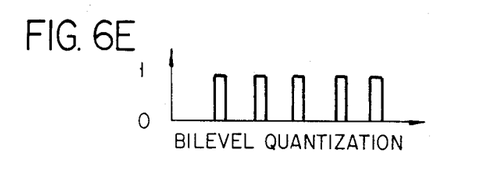

FIG. 5 shows a front view of the X-ray shield member 50. The X-ray shield member 50 is fabricated by a plurality of X-ray shields such as lead pieces 56 and a thin plate-like material such as a synthetic resin film 58. These lead pieces 56 are positioned with equidistance relationship in a matrix in the resin film 58. Each lead pieces 56 has a size of 2 mm×2 mm, for example.

Figure 9:
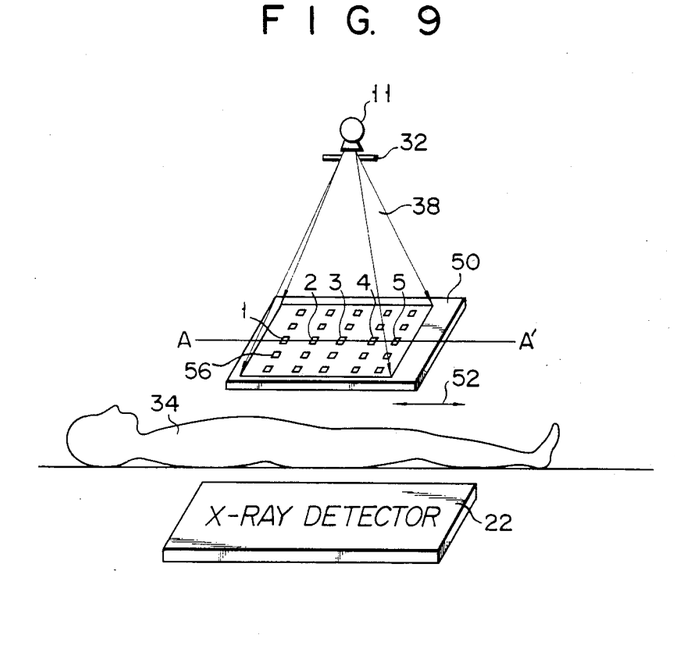
FIGS. 9 and 10 schematically illustrates the scattered X-ray intensity data with respect to the X-ray shield member and the detector.
Figure 10:
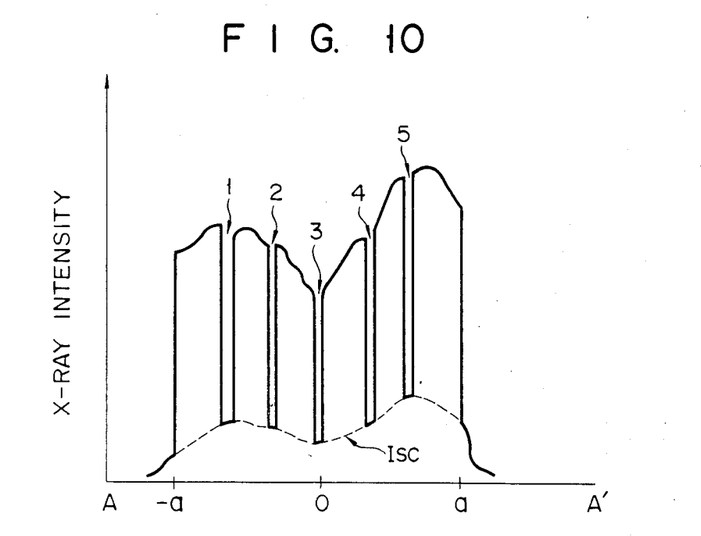

While the X-ray shield member 50 is positioned in the X-ray projection area 38 defined by projecting X-rays from the X-ray source 11 via the collimeter 50 to the X-ray detector 22 through the object 34, the resulting intensity distribution of the transmitted X-ray image signal, obtained by projecting the X-ray toward the object 34, is shown by a graphic representation of FIG. 10. The scattered X-ray intensity distribution Isc represents one which is taken along the lines A—A' on the surface of the X-ray detector 22 (see FIG. 9). As seen from the distribution curve of FIG. 10, the intensity levels of those positions where the lead pieces 56 are positioned (indicated by numerical references 1, 2, 3, 4, and 5) steeply drop. Consequently, these intensity levels indicate the intensity of the scattered X-ray components Isc, because the primary X-ray components are substantially completely blocked by those lead pieces 56.

FIG. 9 is an enlarged drawing for illustrating the relationship between the X-ray shield member 50 and the peripheral components.

It should be noted that the arrangement of the X-ray source 11 and the detector 22 shown in FIG. 9, is reversed, compared with the arrangement shown in FIG. 4, but there is no technical difference between them.

4. OPERATION OF THE APPARUTUS

Operations of the X-ray diagnostic apparatus (100) will now be described with reference to FIGS. 4 to 7.

Referring back to FIG. 4, the X-ray source 11 is energized to project the first X-rays toward the patient 34 while the X-ray shield member 50 is slid along the longitudinal axis (not shown in detail) of the couch 36 and positioned within the X-ray projection area 38 by means of the slide device 54. The slide device 54 is electronically controlled by the system control unit 20. The X-ray transmitted through the patient 34 is incident, as the X-ray image upon the X-ray detector 22. The X-ray image is converted into an analogue X-ray transmission image signal. Thereafter, it is converted by the A/D converter 23 into corresponding digital transmission data (which will be referred to as shielded "X-ray image data"). The shielded X-ray image data is temporarily stored in the first memory 24.

From the digital shielded X-ray image data stored in the first memory 24, the amount of the scattered X-ray components of the portions shielded by the lead pieces 56 can be calculated by the first arithmetic operation device 26 in a given calculation method (which will be described later). The resultant X-ray shield data is stored in the first memory 24. The X-ray shielded data is interpolated to provide scattered X-ray intensity data that represents the intensity distribution of scattered X-ray components for the entire projection area.

After the first X-ray projection with the shield in place, another X-ray projection is excuted after the X-ray shield member 50 has been completely removed from the X-ray projection area 38 by driving the slide device 54. Similarly, X-ray transmission data is acquired and temporarily stored as second X-ray transmission data (which will be referred to as unshielded "X-ray image data") in the second memory 25. Thereafter, both the shielded X-ray image data stored in the first memory 24 and the unshielded X-ray transmission data (Im(x,y)) stored in the second memory 25 are fed to the first arithmetic operation device 26. The functions of this device 26 are as follows.

First, the shielded X-ray image data that has been stored in the first memory 24 is subtracted from the unshielded X-ray image data, thereby obtaining "primarry X-ray intensity data" of the portions within the X-ray projection area 38 which are shielded by the lead pieces 56. Second, another subtraction is carried out between the unshielded X-ray original image data and the scattered X-ray intensity data of (as will be describd later).

The above-described primary X-ray intensity data derived from the first arithmetic operation device 26 is transferred to the second arithmetic operation device 27 via the data bus 40. In the second arithmetic operation device 26, the primary X-ray intensity data is bilevel-quantized in such a way that for example, a certain intensity level is converted into a digital "1" level (corresponding to the portion that is shielded by the lead piece 56), and an intensity level higher than the threshold level is converted into a digital "0" level (corresponding to the portions that are not shielded, or substantially not shielded by the lead piece 56).

5. BILEVEL QUANTIZATION

The bilevel quantization will now be described in more detail.

FIG. 6 shows an enlarged signal waveform of the shielded X-ray image data and unshielded X-ray image data in relation to the position of the lead piece 56. The subtraction of the shielded X-ray image data of FIG. 6B from the unshielded X-ray image data of FIG. 6C results in obtaining the primary X-ray intensity data of FIG. 6D. The X-ray shielded data of the portions which is not shielded by the lead piece 56 has a higher level and than the threshold level is converted into the digital "0" level signal. The X-ray shielded data of the portion which is shielded by the lead piece 56 has a lower level than the threshold level is converted into the digital "1" level signal. This level conversion is called "the bilevel quantization". This bilevel quantization is carried out in the second arithmetic operation device 27. As seen from FIG. 6C, in general, the waveform of the shielded X-ray image data is distorted and stretched. It is therefore necessary to distinguish the desirable signal belonging to the shielded portion (i.e., the X-ray shielded data) from the signal belonging to the other portion (i.e., the primary X-ray signal and a part of the scattered X-ray signal). As a result, the 1-level signal identifies only the scattered X-ray components caused by the corresponding lead piece 56 in the X-ray shield member 50. (see FIG. 6E).

6. CALCULATION OF SCATTERED X-RAY

The resultant bileveled data of the second arithmetic operation device 27 is fed via the data bus 40 to the system processing unit 20. In this unit 20, central addresses and distances between the adjoining central addresses having the above 1-level signal with respect to the entire memory region of the first memory 24, and average valves of the X-ray shielded data of the X-ray shielded region are obtained by utilizing the X-ray shielded data which has been stored in the first memory 24. The average valves of the X-ray shielded data are so-called "scattered X-ray data". It is apparent that this system processing unit 20 also performs the sequence control of the entire system 100.

Thus, the scattered X-ray data of the system processing unit 20 is transferred via the data bus 40 to the third arithmetic operation device 28 in combination with the data relating to the portion which is shielded by the lead piece 56, i.e., the central addresses and the distances for the X-ray shielded portions. In the third arithmetic operation device 28, an interpolation operation is effected by way of a SINC function (a sampling function) by receiving the data of the central addresses and the distances derived from the system processing unit 20 and also addresses of the respective pixels of the memories. As a result, the desirable scattered X-ray intensity data Isc(x, y) (see formula (1)), over the entire X-ray projection area 38 can be calculated in the third arithmetic operation device 28.

The scattered X-ray intensity data Isc(x, y) over the entire X-ray projection area 38 is sent via the data bus 40 to the first arithmetic operation device 26. In the first arithmetic operation device 26, the unshielded X-ray image data Im(x, y) which has been previously stored in the second memory 25 is subtracted from the scattered X-ray intensity data Isc(x, y), so that the primary X-ray data Ip(x, y) can be obtained therein. In other words, formula (1) is calculated in the first arithmetic operation device 28.

Thereafter, the primary X-ray data Ip(x, y) is A/D-converted into the corresponding analogue signal in the D/A converter 21. The converted primary X-ray signal is fed to the TV monitor 29 and also the imager 30 for displaying and recording the X-ray transmission image of the object 34 having no adverse effects of the scattered X-ray components.

7. FUNCTIONS OF ARITHMETIC OPERATION DEVICES

The functions of the major circuit components will now be summarized.

The first arithmetic operation device 26 performs the first subtraction between the shielded X-ray image data stored in the first memory 24 and the unshielded X-ray image data Im(x, y) stored in the second memory 25, thereby deriving the X-ray intensity data of the portions within the primary X-ray projection area which are shielded by the lead pieces 56 (i.e., the intensity data for the primary X-rays of the shielded portion), and the second subtraction is effected between the above-described unshielded X-ray image data and the scattered X-ray intensity data Isc(x, y) over the entire projection area which is derived from the third arithmetic operation device 28, thereby obtaining X-ray transmission data from which adverse effects by the scattered X-rays have been eliminated.

The second arithmetic operation device 27 performs the bilevel quantization to the intensity data (digital signal) for the primary X-rays of the shielded portions, thereby discriminating the scattered X-ray intensity data of the shielded portions from the X-ray intensity data of the non-shielded portions.

The system processing unit 20 processes the bileveled intensity data and also the shielded X-ray image data to obtain central addresses of the respective shielded portions with respect to the memory region of the first memory means 24 and also addresses indicating distances between the adjoining central addresses thereof, and the average value of the scattered X-ray data for the shielded portions.

The third arithmetic operation device 28 performs the data interpolation by the SINC function on the average value of the scattered X-ray data for the shielded portions by utilizing the central addresses, distances and addresses for the respective pixels, thereby obtaining the scattered X-ray intensity data Isc(x, y) over the entire X-ray projection area 38.

8. DETAILED OPERATION OF 3RD ARITHMETIC OPERATION DEVICE

A description will now be made of the operations of the third arithmetic operation device 28 in more detail.

As previously described, the major function of this device 28 is to execute the interpolation of the scattered data based upon the sampling function, i.e., a SINC function.

This is represented by the following equation;

$$S(x, y) = \sum_{n_1=-\infty}^{\infty} \sum_{n_2=-\infty}^{\infty} S(n_1 X, n_2 Y) \cdot \qquad (2)$$

$$\frac{\sin\left[\frac{2\pi}{X}(x-n_1X)/2\right]}{\frac{2\pi}{X}(x-n_1X)/2} \cdot \frac{\sin\left[\frac{2\pi}{Y}(y-n_2Y)/2\right]}{\frac{2\pi}{Y}(y-n_2Y)/2}$$

Where $S(x, y)$ denotes the addresses $(x, y)$ of the memory, $S(n_1X, n_2Y)$ indicates the addresses $(n_1X, n_2Y)$ of the portion in the memory, which is shielded by the lead piece 56, X represents the distance between the adjoining lead pieces 56 with respect to the memory in the horizontal direction, and Y represents the distance between the adjoining lead pieces 56 with respect to the memory in the vertical direction. Equation 1 implies that the intensity of the scattered X-ray at a certain memory address can be given by the function of the type of $(\sin Z)/Z$ (so-called "sampling function"), and also the intensity of the scattered X-ray which has been acquired in the equidistance relation. That is to say, the scattered X-ray intensity $S(x, y)$ at a certain memory address (in the first memory 24) is represented by the equidistantly-acquired intensity data;

$$\sum_{n_1=-\infty}^{\infty} \sum_{n_2=-\infty}^{\infty} S(n_1X, n_2Y)$$

multiplied by the SINC function;

$$\frac{\sin\left[\frac{2\pi}{X}(x-n_1X)/2\right]}{\frac{2\pi}{X}(x-n_1X)/2} \cdot \frac{\sin\left[\frac{2\pi}{Y}(y-n_2Y)/2\right]}{\frac{2\pi}{Y}(y-n_2Y)/2}.$$

It is understood from the foregoing that the scattered X-ray intensity data for the intermediate portions surrounded by the shielded portions can be directly calculated from the above SINC function method. However, such an interpolation calculation cannot be directly applied to the remaining pixels located outside the corner portions, e.g., the portions corresponding to the lead pieces 1 and 5 shown in FIG. 9. Accordingly, the interpolation data for these outside portions may be substituted by those for the corner portions. As a result, the entire intensity amounts of the scattered X-rays can be calculated for the storage region of the first memory 24 ($512 \times 512$ pixel numbers), whereby the desired spatial distribution of the scattered X-ray intensity $Isc(x, y)$ over the entire projection area 38 can be obtained.

9. INTERNAL CIRCUIT DIAGRAM OF 3RD ARITHMETIC OPERATION DEVICE

A detailed description will now be made of the internal circuit diagram of the third arithmetic operation device 28 by which the data interpolation by the sampling function is performed.

Figure 7:
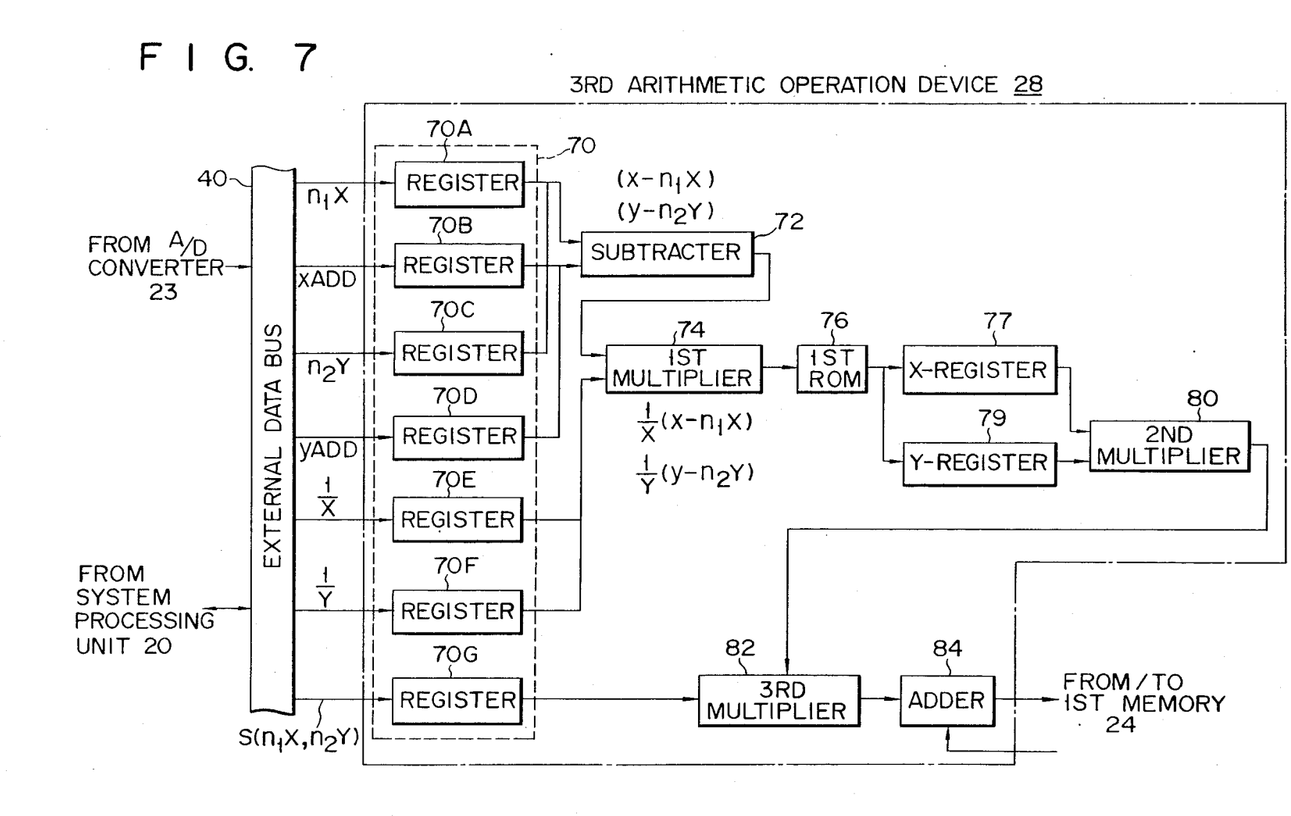
FIG. 7 shows a block diagram of the third arithmetic operation device of FIG. 4.

FIG. 7 shows a block diagram of the fundamental circuit of the third arithmetic operation device 28. As an input of the device 28, there is provided a register unit 70. The register unit 70 is constructed by seven registers 70A to 70G. These registers 70A to 70G temporarily hold the X-ray shielded data, the intensity data of the scattered X-ray, and the address data of the respective pixels in the memory region of the first memory 24 (see FIG. 4). These data are fed from the other circuit elements via the external data bus 40. For example, the address data for the X direction xADD is fed from the system processing unit 20 via the data bus 40 to the second register 70B.

A subtracter 72 is connected to the first and second registers 70A and 70B, which temporarily store the data $n_1X$ and xADD, respectively. The subtracter 72 subtracts two sets of these data to obtain $(x-n_1X)$. Similarly, since the subtracter 72 is connected to the third and fourth registers 70C and 70D, another subtraction is carried out between the data $n_2Y$ and yADD to obtain $(y-n_2Y)$. The data yADD denotes the address in the Y direction. A first multiplier 7 is connected, on one hand, to the output of the subtracter 72 and, on the other hand, to the fifth and sixth register 70E and 70F. First, this register 7 multiplies the subtracted data $(x-n_1X)$ by $1/X$ which is held in the fifth register 70E, thereby obtaining:

$$1/X \cdot (x-n_1X) \tag{3}$$

Second, it multiplies the subtracted data $(y-n_2Y)$ by $1/Y$ which is temporarily stored in the sixth register 70F, thereby obtaining:

$$1/Y \cdot (y-n_2Y) \tag{4}$$

A first Read Only Memory (ROM) 76 as a conversion table is connected to the first multiplier 74. When one multiplied result $(1/X \cdot (x-n_1X))$ is input from the multiplier 74 to the first ROM, the following value is derived therefrom by means of the conversion table:

$$\frac{\sin\left[\frac{2\pi}{X}(x-n_1X)/2\right]}{\frac{2\pi}{X}(x-n_1X)/2} \tag{5}$$

When the other multiplied result $(1/Y \cdot (y-n_2Y))$ is input from the multiplier 74 to the first ROM, the following value is output therefrom by means of the conversion table:

$$\frac{\sin\left[\frac{2\pi}{Y}(y-n_2Y)/2\right]}{\frac{2\pi}{Y}(y-n_2Y)/2} \tag{6}$$

X-register 77 and Y-register 79 connected parallel thereto are connected to the output of the first ROM 76 so as to hold the converted values denoted by the equations (5) and (6), respectively.

A second multiplier 80 is connected to the X-register 77 and Y-register 79 so as to multiply the above-mentioned two values by each other. Thereafter, the resultant value of the second multiplier 80 is again multiplied in a third multiplier 82 by the data $S(n1X, n2Y)$ which is held in the seventh register 70G, thereby obtaining:

$$S(n_1X, n_2Y) \frac{\sin\left[\frac{2\pi}{X}(x-n_1X)/2\right]}{\frac{2\pi}{X}(x-n_1X)/2}. \tag{7}$$

-continued $$\frac{\sin\left[\frac{2\pi}{Y}(y - n_2Y)/2\right]}{\frac{2\pi}{Y}(y - n_2Y)/2}$$

An adder 84 is connected to the output of the third multiplier 82 so as to add the finally-multiplied value as indicated in the above value (7) to the X-ray shield data which has been stored in the first memory 24. The resultant value of this adder 84 is then stored in the first memory 24.

10. ENTIRE OPERATION OF EMBODIMENT

Figure 8:
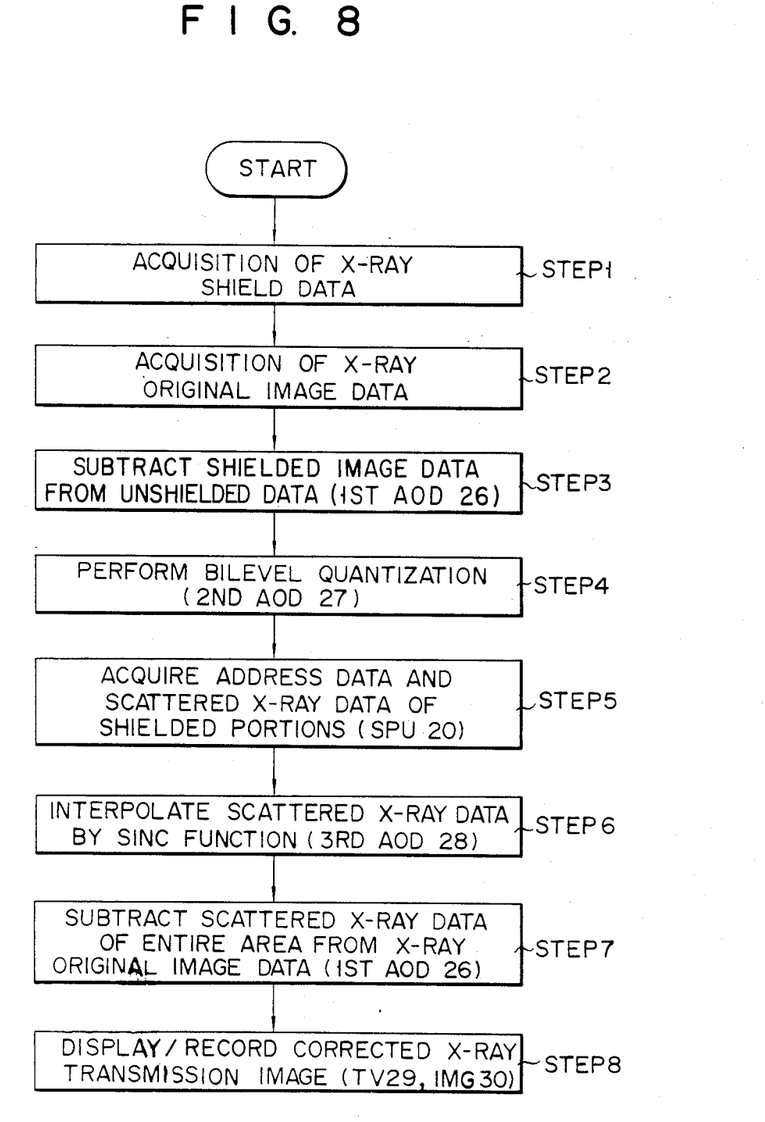
FIG. 8 is a flow chart of the entire operation of the apparatus shown in FIG. 4.

The entire operation of the X-ray diagnostic apparatus 100 will now be summarized with reference to the relevant figures and the flow chart of FIG. 8.

After the X-ray shield member 50 is inserted into the X-ray projection area 38, the first X-ray is projected toward the object 34 to acquire the shielded X-ray image data by the detector 22 and A/D converter 23 (step 1). That is, the first X-ray generated from the X-ray source 11 is transmitted through the X-ray shield member 50 and object 34 and received by the detector 22. The detected signal is converted into the digital shielded X-ray image data that implies the X-ray intensity of the scattered X-rays relating to the X-ray shielded portions (corresponding to the lead pieces 56). This shielded X-ray image data is temporarily stored in the first memory 24.

A further detailed explanation will now be given to the shielded X-ray image data. As shown in FIG. 9, while the X-ray shield member 50 is positioned in the X-ray projection area 38, the X-ray is projected toward the object 34. The X-ray intensity distribution of the shielded X-ray image data is represented in FIG. 10. This distribution data is taken along the line A—A' of FIG. 9. As easily seen from the X-ray intensity data of FIG. 10, the respective values as indicated by 1 to 5 remarkably drop. These portions correspond to those which are shielded by the lead pieces 56. Accordingly, these intensity values are the scattered X-ray data Isc of the shielded portions, because the primary X-rays have been cut by the lead pieces 56.

It should be noted that the shielded X-ray image data include not only the above intensity values of the scattered X-rays but also those of the primary X-rays.

After the acquisition of the shielded X-ray image data is accomplished, the X-ray shield member 50 is removed away along the arrow 52 from the X-ray projection area 38 by the slide device 54. Then the second X-ray projection is carried out to acquire the unshielded X-ray image data (step 2). The unshielded X-ray image data is temporarily stored in the second memory 25.

In step 3, a first digital subtraction is performed between the unshielded X-ray image data stored in the first memory 24 and the shielded X-ray image data stored in the second memory 25. This digital subtraction is carried out in the first arithmetic operation device 26. As a result, only the X-ray intensity values of the primary X-rays can be obtained because, as previously described, the values on the primary X-rays (the portions not shielded by the lead pieces 56) are subtracted from the unshielded X-ray image data.

In step 4, the first subtracted values $(x - n_1X, y - n_2Y)$ are bilevel-quantized in the second arithmetic operation device 27. Since the bilevel quantization has been explained with reference to FIG. 6, no further explanation is made here. By the bilevel quantization, for instance, the portions having a given intensity value of the primary X-rays are denoted by 1-level signal, and the remaining portions are indicated by 0-level signal, so that the 1-level portions correspond to the portions which are shielded by the lead pieces 56.

The bilevel-quantized data obtained in step 4 is fed via the data bus 40 to the system processing unit 20 so as to obtain the desirable address data for the shielded portions of the shielded X-ray image data and also the entire intensity data of the scattered X-ray Isc(x, y) in step 5. The system processing unit 20 processes the bilevel-quantized data (FIG. 6C) to obtain the central addresses of the portions which are shielded by the lead pieces 56, and also the distances between the adjoining the central addresses with respect to the memory region of the first memory 24. This unit 20 also processes to obtain the intensity data of the scattered X-ray in the above-mentioned portions based upon the shielded X-ray image data which has been stored in the first memory 24.

Both the address data and the X-ray shielded data of the scattered X-rays with respect to the portions which are shielded by the lead pieces 56 (in step 5) are input via the data bus 40 to the third arithmetic operation device 28 to be used in the data interpolation by the sampling function, i.e., the SINC function (step 6).

As previously described in (8) DETAILED OPERATION OF 3RD ARITHMETIC OPERATION DEVICE, such a data interpolation by the SINC function is accomplished performing equation (2). That is to say, the calculation is excuted for the entire addresses (x, y) of the memory region (the first memory 24), so that the interpolated value for one set of the X-ray shielded data $S(n_1X, n_2Y)$ can be calculated. Such an arithmetic operation of equation (2) is repeated for all of the X-ray shielded data, with a result that the interpolated intensity data for the respective pixels Isc(x, y) is finally stored in the first memory 24.

In the next step 7, a second digital subtraction is performed between the unshielded X-ray image data acquired in step 2 and the interpolated scattered X-ray intensity data Isc(x, y) acquired in step 6. In other words, the first arithmetic operation device 26 subtracts the interpolated scattered X-ray intensity data of the Isc(x, y) over the entire projection area from the unshielded X-ray image data Im(x, y) so as to obtain the desirable image data containing only the primary X-ray components Ip(x, y) (see equation (1)).

In the final step 8, the desirable X-ray image data having only the primary X-ray components Ip(x, y) is D/A-converted by the D/A converter 21 into the analogue X-ray image signal which is supplied either to the TV monitor 29 to be displayed, or to the imager to be recorded.

In connection with the third arithmetic operation device 28, it is also possible to utilize as independent data the intensity data of the scattered X-ray over the entire projection area Isc(x, y). In this case, this intensity data is derived from the first memory 24 through the data bus 40, which can store at least the intensity data having 1 TV frame capacity.

11. PRACTICAL CIRCUIT OF 3RD ARITHMETIC OPERATION DEVICE

Figure 11:
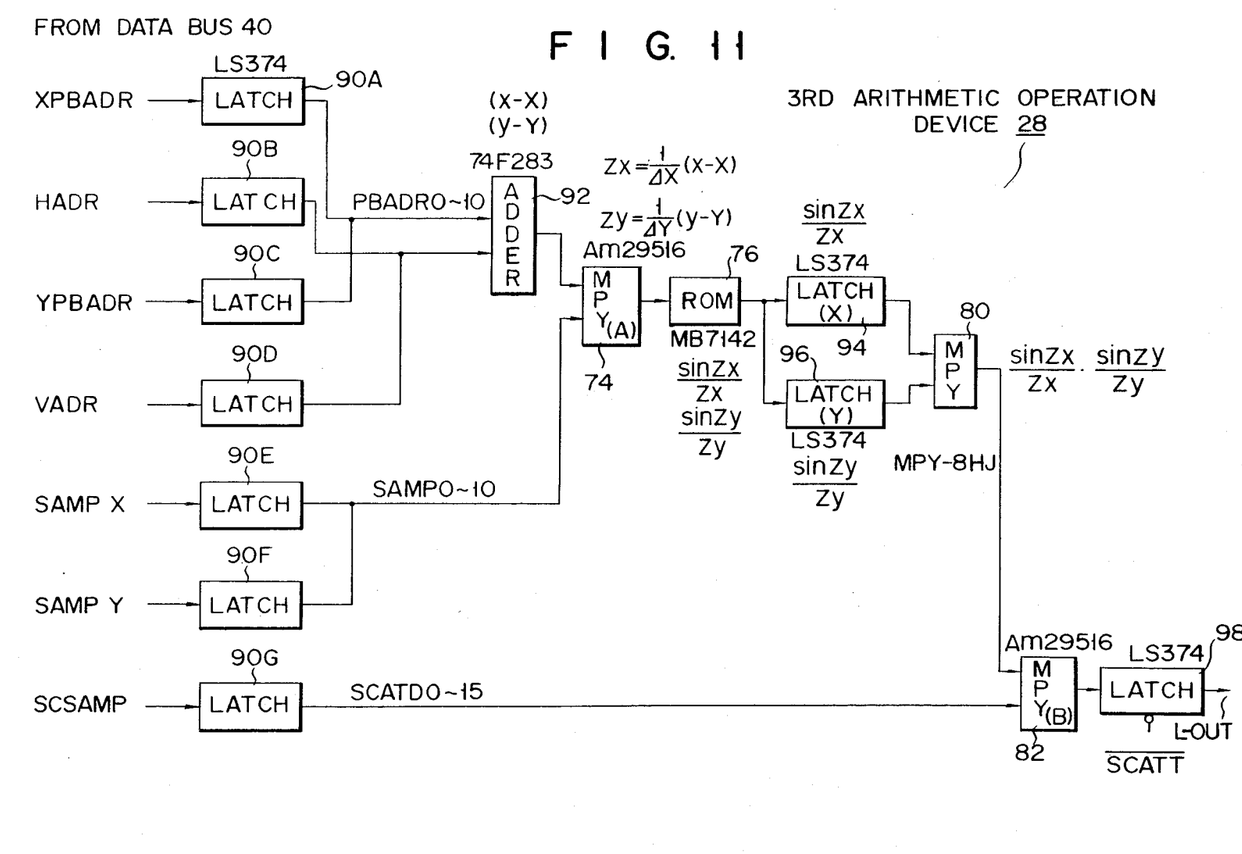
FIG. 11 shows a practical circuit of the third arithmetic operation device.

FIG. 11 shows a block diagram of the practical circuit of the third arithmetic operation device 28. A description of this practical circuit will now be made with reference to FIG. 7.

The registers 70A to 70G of FIG. 7 correspond to latch circuits 90A to 90G of FIG. 11. An adder 92 is employed as the subtracter 72 to add $(x - n_1 X)$ to $(y - n_2 Y)$. It should be noted that in practice the subtraction is effected by this adder 92.

The first multiplier 74, ROM 76, second multiplier 80 and third multiplier 82 are identical to those in FIG. 7. A latch circuit (X) 94 and latch circuit (Y) 96 correspond to the X-register 77 and Y-register 79. Another latch circuit 98 is connected to the output of the third multiplier 82, thereby deriving the output signal L-OUT therefrom.

The circuit elements employed are all commercially available and listed in the following table.

TABLE

| | | |
|---|---|---|
| LATCH 90A to 90G, LATCH(X)(Y), LATCH 98 | SN74LS374N | TI |
| ADDER 92 | 74F283 | Fairchild |
| 1st & 3rd MULTIPLIER 74 | Am29516 | AMD |
| ROM 76 | MB7142 | Fujitsu |
| 2nd MULTIPLIER 80 | MPY-8HJ | TRW |

A description will now be made of a timing chart shown in FIG. 12.

A signal HD has the horizontal (X direction) scanning period (63.5 $\mu$S) with respect to the memory region. A signal $\overline{\text{SCAT H}}$ is a signal to obtain the scattered X-ray signal X in the X direction, and a signal $\overline{\text{SCAT V}}$ is a signal to obtain the scattered X-ray signal Y in the Y direction. A signal VADR is an address signal in the Y direction. A REFERENCE CKC is a reference clock signal having a period of 100 ns.

Figure 12:
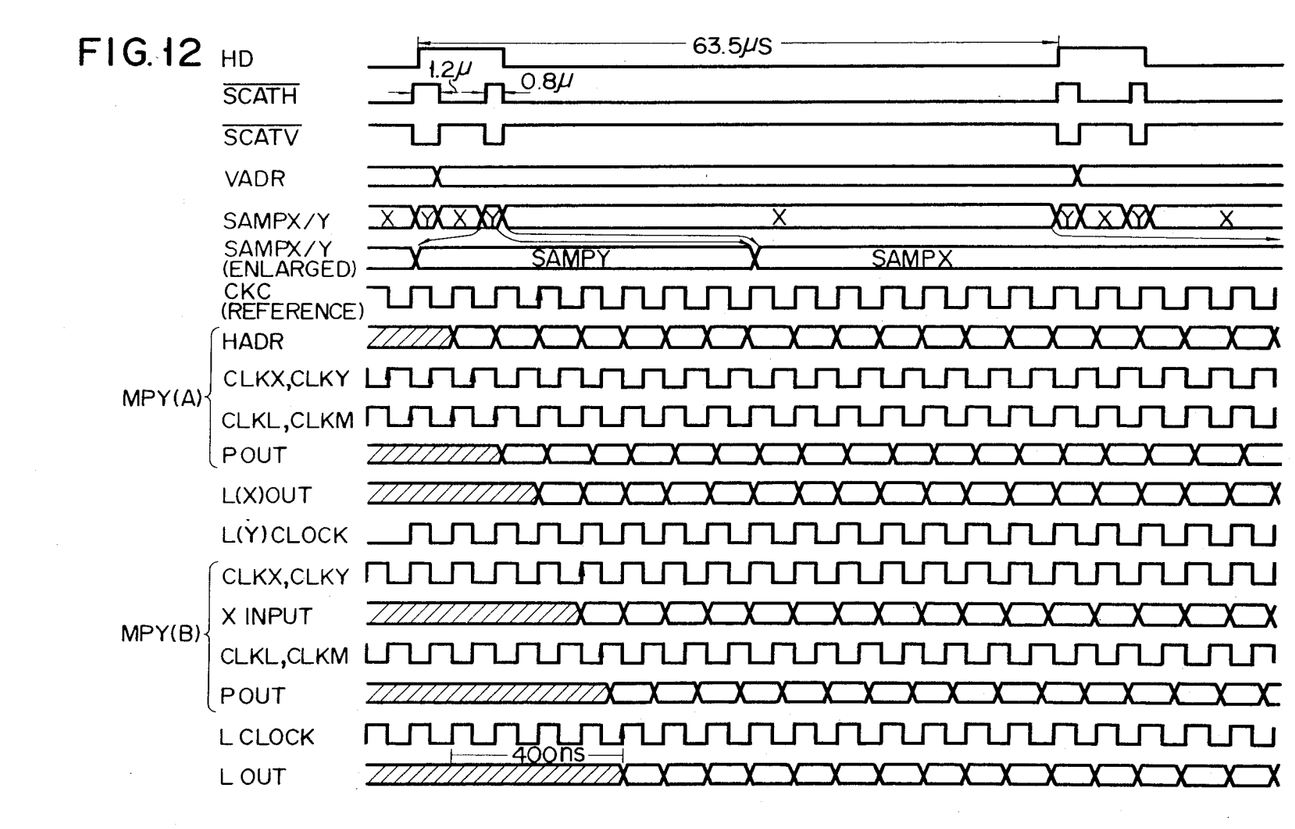
FIG. 12 shows a timing chart of the signals of the circuit shown in FIG. 11.

The respective output signals of the first multiplier 74 (MPY(A)) and of the second multiplier 82 (MPY(B)) are represented under a given timing in FIG. 12. A signal L-OUT is an output signal of the final latch circuit 98. This output signal L-OUT has a delay of 400 ns.

In accordance with the present invention various advantage can be realized.

The X-ray image data containing only the primary X-ray components can be obtained by subtracting the interpolated intensity data of the scattered X-rays from the X-ray original image data which is taken without using the X-ray shield member. The scattered X-ray intensity data is interpolated by utilizing the sampling function.

As a result, it is possible to provide the X-ray diagnostic apparatus by which the X-ray images of the X-ray scanned object can be displayed, whose contrast and sharpness are remarkably improved. It can also contribute to the quantative analysis on the medical image data.

While the present invention has been described using a specific embodiment, it should be understood that further modifications and changes can be made without departing from the scope of the present invention.

For example, in the previous embodiment as shown in FIG. 4, the second arithmetic operation device 27 was employed to perform the bilevel quantization to the intensity data of the primary X-ray for the portions which are not shielded by the lead pieces 56. However, it is possible to omit the second arithmetic operation device 27.

Further, it is not necessary to obtain the average value of the scattered X-ray data for the shielded portions in the system processing unit 20. That is to say, in the previous embodiments the central addresses of the bilevel-quantized data (1-level signal) were utilized as the data indicating the shielded portions. However, it is not absolutely necessary to employ such central addresses, but to utilize the other addresses.

It is also possible to construct a single operation unit to combining all of the arithmetic operations of the first to third devices 26, 27 and 28. Also a single memory can be realized instead of the first and second memories 24 and 25.

What is claimed is:

1. An X-ray diagnostic apparatus comprising:

X-ray source means for generating X-rays;

X-ray detection means for detecting an X-ray image of an object under examination by projecting said X-rays from said X-ray source toward said object over an X-ray projection area and for converting a resultant detected image into X-ray transmission signals;

analog-to-digital converter means for converting said X-ray transmission signals into corresponding digital X-ray transmission data;

X-ray shield member means, having a plurality of X-ray shields, for selectively blocking the transmission of said X-rays from said X-ray source means to said X-ray detection means through said object for selected blocked portions of said projection area;

first memory means for temporarily storing first X-ray transmission data acquired from said analog-to-digital converter means with said X-ray shield member inserted into said X-ray projection area;

second memory means for temporarily storing second transmission data acquired from said analog-to-digital converter means with said X-ray shield member removed away from said X-ray projection area; and arithmetic operation means:

(i) for performing a first subtraction between said first X-ray transmission data and said second X-ray transmission data to obtain first X-ray intensity data of said selected blocked portions of said projection area which are shielded by said X-ray shields;

(ii) for performing bilevel quantization to said first X-ray intensity data to obtain bilevel data which identifies those portions of said first X-ray transmission data corresponding to said selected blocked portions of said projection area;

(iii) for obtaining, as a function of said bilevel data, selected data from said selected blocked portions of said first X-ray transmission data;

(iv) for interpolating said selected data over said projection area; and (v) for performing a second subtraction between said second X-ray transmission data and said interpolated selected data to obtain third X-ray transmission data essentially free from scattered X-ray components.

2. An apparatus of claim 1 wherein said arithmetic operation means includes means for obtaining the central addresses of said selected blocked portions from said bilevel data and means for obtaining, as a function of said central addresses, said selected data for the entire areas of said selected blocked portions.

3. An apparatus of claim 1 wherein said arithmetic operation means includes means for obtaining the central addresses of said selected blocked portions from said bilevel data; means for obtaining, as a function of said central addresses, the values of said first X-ray transmission data in the vicinity of said central addresses; and means for obtaining, as a function of the average value of said first X-ray transmission data in the vicinity of said central addresses, said selected data for each of said selected blocked portions.

4. An apparatus of claim 1 wherein said arithmetic operation means includes means for interpolating said selected data by a SINC function over said projection area.

5. An apparatus of claim 1 including means for selectively sliding said X-ray shield member means into said projection area.

6. An apparatus of claim 1 wherein the X-ray shield member means is constructed by a synthetic resin film and said X-ray shields comprise lead pieces equidistantly arranged in a matrix form.

7. An apparatus as claimed in claim 6 wherein each of said lead pieces is a square of $2 \times 2$ millimeters.

* * * * *